United States Patent
Mata

(10) Patent No.: US 11,103,805 B2
(45) Date of Patent: Aug. 31, 2021

(54) SYSTEM AND METHOD FOR FILTERING ORGANIC COMPOUNDS

(71) Applicant: Caleb Mata, Salem, OR (US)

(72) Inventor: Caleb Mata, Salem, OR (US)

(*) Notice: Subject to any disclaimer, the term of this patent is extended or adjusted under 35 U.S.C. 154(b) by 0 days.

(21) Appl. No.: 16/368,456

(22) Filed: Mar. 28, 2019

(65) Prior Publication Data

US 2021/0213373 A1    Jul. 15, 2021

(51) Int. Cl.
*B01D 15/20* (2006.01)
*B01J 20/28* (2006.01)
*C07D 311/80* (2006.01)
*B01J 20/10* (2006.01)
*B01J 20/12* (2006.01)

(52) U.S. Cl.
CPC ............ *B01D 15/20* (2013.01); *B01J 20/103* (2013.01); *B01J 20/12* (2013.01); *B01J 20/28052* (2013.01); *C07D 311/80* (2013.01)

(58) Field of Classification Search
CPC ..................................................... B01D 15/20
USPC ........................................................... 549/390
See application file for complete search history.

(56) References Cited

U.S. PATENT DOCUMENTS 10,894,224 B2 * 1/2021 Mata ....................... C07C 37/70

* cited by examiner

*Primary Examiner* — Taofiq A Solola
(74) *Attorney, Agent, or Firm* — Chernoff, Vilhauer, McClung & Stenzel, LLP

(57) ABSTRACT

A system and method for removing undesirable organic compounds so that the desirable cannabinoids, terpenes, and any other beneficial organic compounds can be easily and effectively captured is provided herein. The system and method makes use of bentonite clay, silica gel and magnesium silicate filters through which a solution containing the organic compounds is rinsed with liquid non-polar solvent. The undesirable components remain in the bentonite clay, silica gel and magnesium silicate while the beneficial organic compounds pass through and are collected in a liquid solution.

13 Claims, 2 Drawing Sheets

SYSTEM AND METHOD FOR FILTERING ORGANIC COMPOUNDS

CROSS-REFERENCE TO RELATED APPLICATIONS

Not applicable.

BACKGROUND OF THE INVENTION

The present invention relates to using bentonite clay, silica gel and magnesium silicate as a filtration medium, and more specifically, the present invention relates to using such filters to extract beneficial organic compounds from plant materials by filtering out the non-desirable compounds such as organic pigments, plant fats, lipids, and other plant cells that are not considered medicinally or industrially valuable. Additionally, the present invention relates to using bentonite bleaching clay, silica gel and magnesium silicate. about 50-75% bentonite clay, 10-25% silica gel, and 10-25% magnesium silicate as a filtration medium.

Bentonite clay, silica gel and magnesium silicate have been used for many years in a number of applications utilizing their absorptive properties and their filtration properties, among other applications.

BRIEF SUMMARY OF THE INVENTION

Solvents such as a liquid non-polar solvent can be used to extract organic compounds from plant-based materials such as various forms of hemp or *Cannabis*. Various types of liquid non-polar solvents that can be used with the present invention include butane, hexane, pentane, heptane, ethanol, mct oil, cold pressed hemp oil, olive oil, benzene, toluene, diethyl ether, chloroform, 1,4 dioxane and other non-polar liquids. Cannabinoids attach to non-polar substances. The processes and apparatus mentioned herein will work with any cannabinoids derived from hemp or *Cannabis* including, but not limited to: thca, delta 9 thc, cbn, cbd, cbg, thcv cbc, cbda, cbdv, as well as any other unnamed, but present, cannabinoid found in hemp or *Cannabis* as long as it is suspended in anything liquid and non-polar.

The desirable components of such an extraction process primarily included cannabinoids or terpenes that can be collected and provided to consumers to aid with numerous medical conditions. Along with the desirable cannabinoids and terpenes there can be a plurality of undesirable compounds that are extracted from the plant matter. These undesirable compounds can include, but are not limited to pigments such as chlorophylls, anthocyanins and carotenoids as well as plant waxes, lipids, or other plant cells that are not considered active ingredients in hemp or cannabinoid products.

The present invention is a system and method for removing these undesirable compounds so that the desirable cannabinoids, terpenes, and any other beneficial organic compounds can be easily and effectively captured.

The equipment used in the invention includes glass Büchner funnels and flasks, and vacuum pumps for suction. But other filtration apparatuses could be used, especially at industrial scale. That is, one could put together similar filtration apparatuses using stainless steel and scale it to any size. Bentonite clay, silica gel and magnesium silicate are placed in the funnel, solution is poured into the funnel and vacuum suction pulls the solution through the bentonite clay, silica gel and magnesium silicate and down into the flask, removing pigments and other compounds. Filtration is repeated until solution is pigment free.

The method of filtration as according to an embodiment of the present invention includes setting up and prepping filters, ideally a plurality of filters are connected to each pump to maximize efficiency of the system. A maximum efficiency state is considered to exist when the maximum number of filters are attached to each pump without detrimentally effecting the suction performance of each pump. The optimal ratio of filters to pumps will vary from embodiment to embodiment.

Before pouring solution into filters, proper dilution of the solution to be filtered is necessary. Ideally the pre-filtration solution should be less than 0.01 g of hemp or *Cannabis* oil per mL to minimize potential yield loss.

Bentonite clay, silica gel and magnesium silicate is placed into filters. It should be noted that on a first pass less filtration medium is used than in subsequent passes.

After proper dilution, turn on vacuum pumps and pack down the bentonite clay, silica gel and magnesium silicate in the filter. Evenly packed bentonite clay, silica gel and magnesium silicate is optimal because it minimizes the solution's ability to find a path of least resistance. The solution is then poured into a filter containing the bentonite clay, silica gel and magnesium silicate and pulled through via vacuum suction. When the solution is almost fully pulled through, meaning a small amount is still in filter, a liquid non-polar solvent rinse is added. The liquid non-polar solvent helps to dissolve and pull through any yield stuck in the bentonite clay, silica gel and magnesium silicate. The rinse process is repeated until the resultant solution is clear.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

DETAILED DESCRIPTION OF THE PRESENT INVENTION

Figure 1:
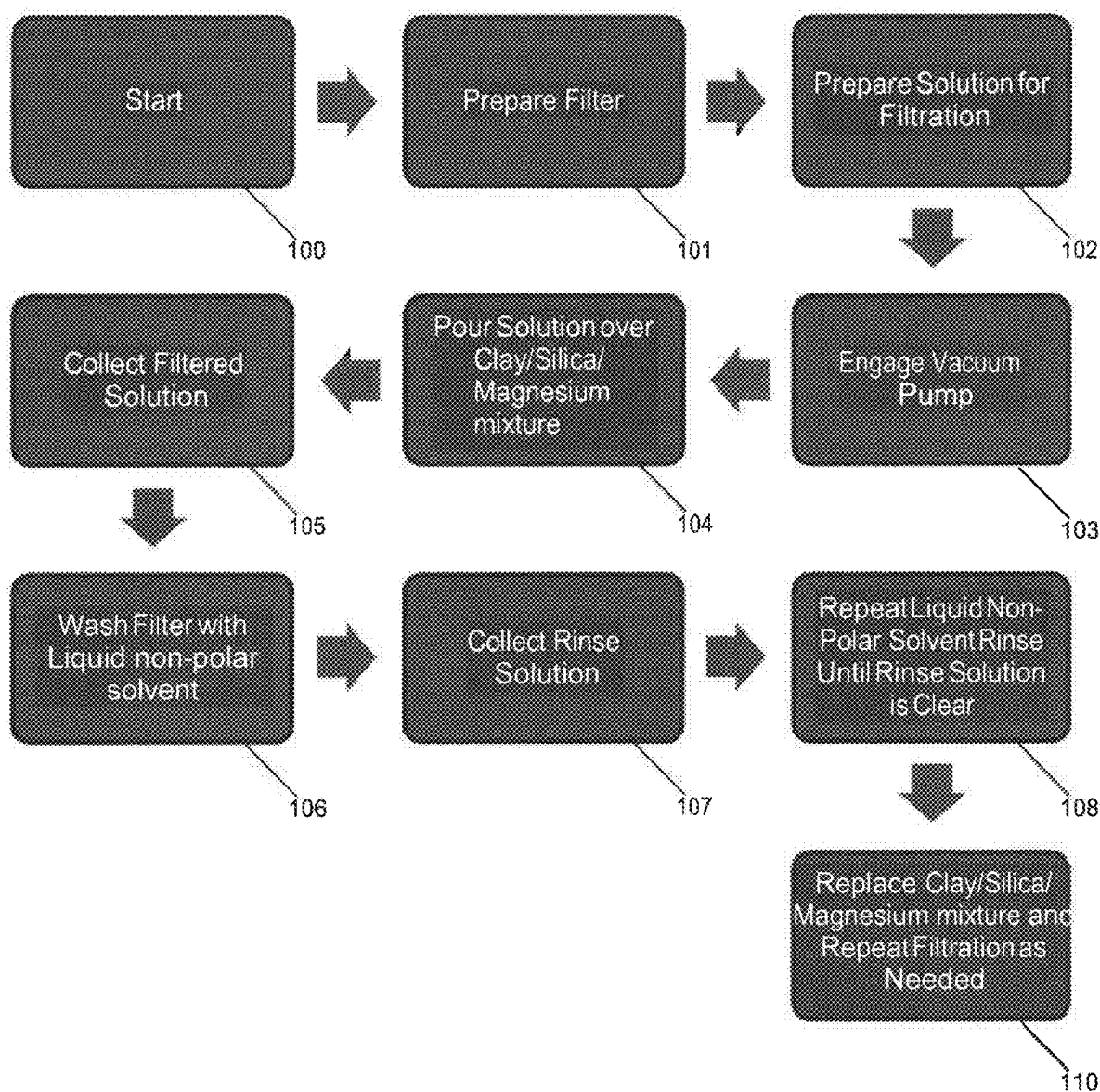
FIG. 1 is a flowchart showing a method for filtering organic compounds using bentonite clay, silica gel and magnesium silicate as according to an embodiment of the present invention.
Figure 2:
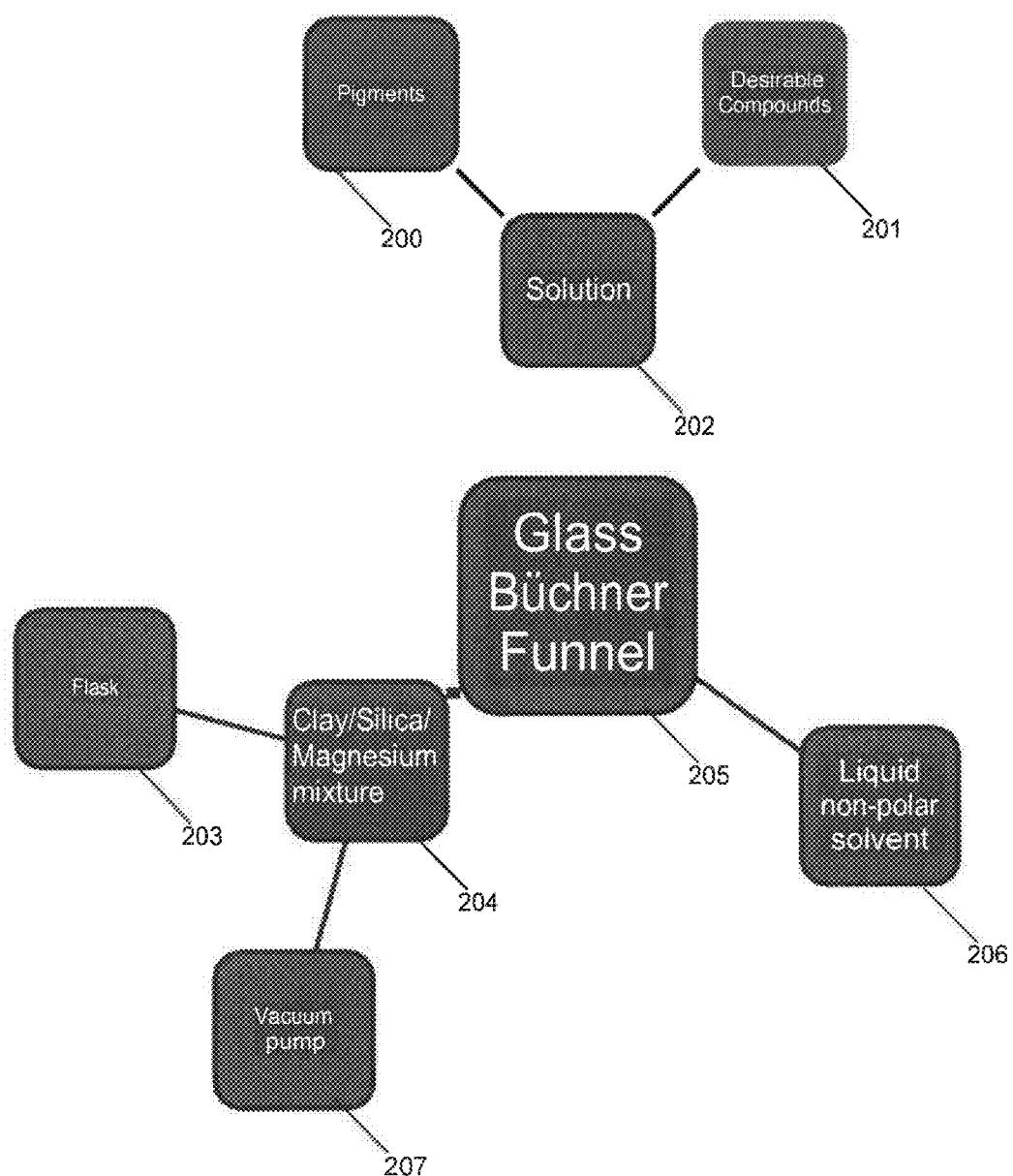
FIG. 2 is a diagram showing the components of a system for filtering organic compounds using bentonite clay, silica gel and magnesium silicate as according to an embodiment of the present invention.

Referring now to FIGS. 1 and 2, the invention comprises a method and system of bentonite clay, silica gel and magnesium silicate filtration. The purpose of the filtration is to remove undesirable compounds (200) from a liquid non-polar solvent solution that are not cannabinoids or terpenes. The cannabinoids and terpenes provide medical benefits and are desirable extraction products of the *Cannabis* plant. The method of filtration described herein starts (100) with preparing the filter (101) that will extract undesirable organic compounds from a solution (202) such as pigments as well as plant waxes, lipids, or other plant cells that are not considered active ingredients in hemp or cannabinoid products (200). The pigments include chlorophyll, anthocyanin and carotenoid. These undesirable compounds have no medical benefit and are undesirable byproducts (200) from the process of extracting cannabinoids (200) and terpenes from *Cannabis* using a liquid non-polar solvent. Liquid non-polar solvents that can be used with the present invention include butane, hexane, pentane, heptane, ethanol, mct oil, cold pressed hemp oil, olive oil, benzene, toluene, diethyl ether, chloroform, 1,4 dioxane and other non-polar liquids.

The filter preparation step (100) comprises preparing at least one filter by placing a filtering device, such as a paper, glass or quartz frit, woven metal, spun or woven rock, clay or cloth filter designed to trap particles roughly the size of bentonite clay, silica gel and magnesium silicate particles and larger, into a filter container. The filter container can be a glass Büchner funnel or could be a larger funnel made of a different material (205). Alternatively, the filter could be a large-scale industrial apparatus such as a 1,000-ton stainless steel reactor half full of bentonite clay, silica gel and magnesium silicate with a large 10,000-liter extraction pump that distributes the entire solution over the filtration material all at one time. Next in the filter preparation step is to attach a vacuum pump (207) and hose lines to the funnel (205) and a receptacle that will catch the filtered solution such as a glass flask (203). Then, bentonite clay, silica gel and magnesium silicate (204) is added to the filter container (205). For the first iteration, a lesser amount of bentonite clay, silica gel and magnesium silicate (204) is desirable whereas subsequent iterations can use greater amounts. It is preferable to evenly pack the bentonite clay, silica gel and magnesium silicate (204) in the funnel (205) so that solution flowing through the bentonite clay, silica gel and magnesium silicate (204) cannot find a path of least resistance and avoid proper filtration. One possible technique for packing the bentonite clay, silica gel and magnesium silicate (204) is to activate the vacuum pump (207) to draw down the bentonite clay, silica gel and magnesium silicate (204) into the funnel (205).

In an embodiment of the present invention, a plurality of filters (205) are connected to each pump (207) so that a maximum number of filters (205) are attached to each pump without detrimentally effecting the suction performance of each pump (207). The optimal ratio of filters (205) to pumps (207) will vary from embodiment to embodiment.

The next step in the process is to prepare the solution for filtration (102). Before filtering, it is necessary to properly dilute the solution (204). Ideally the solution (204) should be thin enough that it is less than 0.01 g/mL of a liquid non-polar solvent (206) to minimize potential yield loss. Dilution is performed by adding a liquid non-polar solvent to the solution. Adding a liquid non-polar solvent also provides the benefit of minimizing the loss of cannabinoids and terpenes. An ideal solution dilution mixture is 0.009 g/mL of a liquid non-polar solvent (206).

It should be noted that the steps of preparing the filter (101) and preparing the solution (102) can be done in any order or simultaneously. It is not essential to embodiments of the present invention that they be performed in the sequential order as shown in FIG. 1.

Once the filter(s) and solution are prepared (101, 102), the vacuum pump (207) is engaged. In an embodiment of the present invention, at least one vacuum pump (207) is attached to at least one funnel (205) containing bentonite clay, silica gel and magnesium silicate (204). In other embodiments of the present invention, a plurality of vacuum pumps (207) are attached to a plurality of funnels (205) with the ratio generally being one vacuum pump (207) for as many funnels (205) as possible without significantly degrading the efficiency or performance of the pump (207). The invention is scalable and can be expanded to meet whatever production capacity is required by adjusting the size of the vacuum, or the size of the filtration apparatus.

After the vacuum pump is engaged (103), the solution to be filtered is poured over the top of the packed bentonite clay, silica gel and magnesium silicate (104) and allowed to flow through to the bottom of the funnel (205). This is the filtration step and it can be repeated with the liquid non-polar solvent rinse, described below, as many times as required. The first filtration step (104) is performed with a lesser amount of bentonite clay, silica gel and magnesium silicate (204) because of the high wax content of the crude solution. The greater the wax content, the greater the loss of the desirable organic compounds (201). The desirable organic compounds (201) are the cannabinoids and terpenes. The exact amount of diatomaceous (204) earth used during filtration varies from embodiment to embodiment based on the scale of the filtering system. Larger apparatus and pumps will allow for greater amounts of bentonite clay, silica gel and magnesium silicate mixture (204) to be used.

The resultant solution from step (104) is collected in a receptacle such as a glass flask (105). This is the collection step that captures the filtered solution that should contain very little to no undesirable compounds (200). If the solution was properly prepared in step (102), then substantial amounts of desirable compounds (201) will be collected without the filter becoming clogged.

To extract additional amounts of desirable compounds (201), the bentonite clay, silica gel and magnesium silicate can be rinsed with a liquid non-polar solvent (106). The term "rinse" and "wash" can be used interchangeably to describe the process of adding additional amounts of a liquid non-polar solvent (206) to the bentonite clay, silica gel and magnesium silicate (204) through which the solution that was filtered.

The rinsed solution is collected (107) and the rinse step (106) can be repeated as many times as necessary. Optimally, the rinse step (106) will be repeated until the solution exiting the filter is clear (108).

The bentonite clay, silica gel and magnesium silicate can be replaced (110) and the entire filtration process repeated (103-110) as many times as necessary.

Parameters that affect the efficiently of the filtration process include the suction power of the vacuum pump (207), the amount of the bentonite clay, silica gel and magnesium silicate (204) placed in the filter (205), and the initial dilution of the crude solution. The crude solution is considered to be the solution that is to be filtered (202) prior to it being filtered.

In a preferred embodiment of the present invention, for every 1 unit of crude solution (202) approximately 1.6 to 3.8 units of bentonite clay, silica gel and magnesium silicate (204) is used while 3.3 to 8 units of a liquid non-polar solvent such as butane, hexane, pentane, heptane, ethanol, met oil, cold pressed hemp oil, olive oil, benzene, toluene, diethyl ether, chloroform, 1,4 dioxane and other hydrocarbon oils (206) is required. The primary factors that change the amount of bentonite clay, silica gel and magnesium silicate (204) and a liquid non-polar solvent (206) required are the strain of the *Cannabis* being filtered and the age of the crude solution (202). The number of rinse steps (108) required varies depending on the amount of desirable compound (201) yield per run.

In a preferred embodiment of the present invention, approximately 1.6 to 3.8 times more bentonite clay, silica gel and magnesium silicate (204) than crude solution is used in every filter (205). A crude solution containing a ratio of a liquid non-polar solvent (206) to desirable compounds (201) is 0.001 g/mL to 0.009 g/mL. At this ratio, the bentonite clay, silica gel and magnesium silicate (204) can effectively pull out high concentrations of undesirable compounds (200) from the crude solution (202) due to lower PPM measurements of the undesirable compound (200). The crude solution contains cannabinoids that contain, but are not limited to: thca, delta 9 the, cbn, cbd, cbg, thcv cbc, cbda, cbdv, as well as any other unnamed, but present, cannabinoid found in hemp or *Cannabis* as long as it is suspended in anything liquid and non-polar.

Unless otherwise defined, all technical and scientific terms used herein have the same meaning as commonly understood by one of ordinary skill in the art to which this invention belongs. Although methods and materials similar to or equivalent to those described herein can be used in the practice or testing of the symmetrical measuring tool, suitable methods and materials are described above. All publications, patent applications, patents, and other references mentioned herein are incorporated by reference in their entirety to the extent allowed by applicable law and regulations. The symmetrical measuring tool may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

It should be noted that for purposes of this Description, the terms "diatomaceous earth", "bentonite", "silica gel", and "magnesium silicate" can be used interchangeably to refer to the filtration medium through which the crude solution is filtered. None of the embodiments of the present invention are intended to limit the filtration medium to one specific substance. Furthermore, the present invention contemplates using mixtures of the aforementioned substances in some embodiments.

I claim:

1. A method for filtering out undesirable organic compounds comprising; preparing bentonite clay, silica gel and magnesium silicate filter;
   preparing a crude solution by diluting the crude solution with a liquid non-polar solvent;
   attaching a vacuum pump to the bentonite clay, silica gel and magnesium silicate filter;
   pouring the diluted crude solution into the bentonite clay, silica gel and magnesium silicate filter;
   causing the vacuum pump to draw the diluted crude solution through the bentonite clay, silica gel and magnesium silicate filter;
   collecting the filtered crude solution;
   washing the bentonite clay, silica gel and magnesium silicate filter by pouring a liquid non-polar solvent into the bentonite clay, silica gel and magnesium silicate filter;
   collecting the liquid non-polar solvent that was used to wash the bentonite clay, silica gel and magnesium silicate filter; and
   performing the step of washing the bentonite clay, silica gel and magnesium silicate filter by pouring the liquid non-polar solvent into the bentonite clay, silica gel and magnesium silicate filter and the step of collecting the liquid non-polar solvent that was used to wash the bentonite clay, silica gel and magnesium silicate filter at least one additional time.

2. The method of claim 1 further comprising replacing the bentonite clay, silica gel and magnesium silicate filter and repeating the remaining steps of the method at least once.

3. The method of claim 1 wherein the crude solution is diluted to a range between 0.01 g/mL liquid non-polar solvent and 0.001 g/mL liquid non-polar solvent.

4. The method of claim 1 further comprising attaching a plurality of bentonite clay, silica gel and magnesium silicate filters to the vacuum pump.

5. The method of claim 1 further comprising washing the bentonite clay, silica gel and magnesium silicate filter by pouring liquid non-polar solvent into the bentonite clay, silica gel and magnesium silicate until the resultant mixture is clear.

6. The method of claim 1 claim wherein the bentonite clay, silica gel and magnesium silicate filter is prepared by evenly packing the bentonite clay, silica gel and magnesium silicate into a funnel.

7. The method of claim 1 wherein the undesirable organic compounds are pigments.

8. A system for filtering organic compounds comprising:
   a filter configured to hold bentonite clay, silica gel and magnesium silicate, the filter having a filter component that catches and prevents bentonite clay, silica gel and magnesium silicate from exiting the filter;
   a receptacle to catch a crude solution;
   a vacuum pump attached to the filter and to the receptacle, the vacuum pump operating to draw the filtered solution through the filter during operation of the system; and
   a liquid non-polar solvent solution that is operable to rinse the bentonite clay, silica gel and magnesium silicate after the crude solution is passed through the filter.

9. The system of claim 8 further comprising a second receptacle to catch the liquid non-polar solvent solution that is operable to rinse the bentonite clay, silica gel and magnesium silicate earth.

10. The system of claim 8 wherein the filter is a glass Büchner funnel.

11. The system of claim 8 further comprising a plurality of filters that are attached to the vacuum pump.

12. The system of claim 8 wherein the receptacle for catching the crude solution is a glass flask.

13. The system of claim 8 wherein the vacuum pump is attached to the filter and to the receptacle by way of vacuum tubes.

* * * * *

UNITED STATES PATENT AND TRADEMARK OFFICE
CERTIFICATE OF CORRECTION

PATENT NO. : 11,103,805 B2
APPLICATION NO. : 16/368456
DATED : August 31, 2021
INVENTOR(S) : Caleb Mata It is certified that error appears in the above-identified patent and that said Letters Patent is hereby corrected as shown below:

In the Specification

At Column 5, Line 12: Replace "the" with --thc--.

Signed and Sealed this
Fifteenth Day of November, 2022

Katherine Kelly Vidal
*Director of the United States Patent and Trademark Office*